United States Patent [19]

Pawloski et al.

[11] Patent Number: 5,104,559
[45] Date of Patent: Apr. 14, 1992

[54] HYDROGEN PERFLUOROALKYLAROMATIC ETHERS AND RELATED COMPOSITIONS AND METHODS

[75] Inventors: Chester E. Pawloski, Bay City; Muthiah N. Inbasekaran, Midland, both of Mich.

[73] Assignee: The Dow Chemical Company, Midland, Mich.

[21] Appl. No.: 617,748

[22] Filed: Nov. 26, 1990

[51] Int. Cl.$^5$ .................... C10M 135.28; C07C 41/00
[52] U.S. Cl. ........................................ 252/48.4; 252/54; 568/33; 568/49; 568/52; 568/53; 568/54; 568/332; 568/586; 568/588; 568/635; 568/647; 568/645
[58] Field of Search ............ 252/48.4, 54; 568/637, 568/33, 49, 52, 53, 54, 332, 586, 588, 635, 647, 645

[56] References Cited

U.S. PATENT DOCUMENTS

| | | | |
|---|---|---|---|
| 3,265,741 | 8/1966 | Sheppard | 252/54 |
| 4,024,192 | 5/1977 | Benninger et al. | 252/54 |
| 4,484,008 | 11/1984 | Cook, Jr. et al. | 568/33 |
| 4,792,635 | 12/1988 | Marhold et al. | 568/332 |

FOREIGN PATENT DOCUMENTS

| | | | |
|---|---|---|---|
| 0084743 | 8/1983 | European Pat. Off. | 568/33 |
| 3836175 | 5/1990 | Fed. Rep. of Germany | 568/54 |

*Primary Examiner*—Prince Willis, Jr.
*Assistant Examiner*—Ellen McAvoy

[57] ABSTRACT

A lubricating compound having the structure:

$$R^1-R_f-O-Ar-R^2$$

wherein $R^1$ is a monovalent radical selected from the group consisting of fluoride, unsubstituted aryloxys, substituted aryloxys, unsubstituted arylthios, substituted arylthios, perfluoroalkoxys, and perfluoro (3,6-dimethyl-1, 4-dioxanyl-2-oxy), $R^2$ is a monovalent radical selected from the group consisting of hydrogen, halides, cyano, nitro, unsubstituted alkyls having from 1 to 10 carbon atoms inclusive, perfluoroalkyls having from 1 to 10 carbon atoms inclusive, perfluoroalkoxys having from 1 to 10 carbon atoms inclusive, substituted and unsubstituted hydrogen perfluoroalkoxy aryloxys, substituted and unsubstituted hydrogen perfluoroalkoxy arylthios, unsubstituted alkoxys having from 1 to 8 carbon atoms inclusive, unsubstituted aryls, substituted aryls, unsubstituted aryloxys, substituted aryloxy, unsubstituted alkylthios, substituted arylthios, unsubstituted arylthios, substituted and unsubstituted arylketones, substituted and unsubstituted arylsulfones, and substituted and unsubstituted alkylcarboxys, $R_f$ is a hydrogen perfluoroalkyl divalent radical having from 2 to 10 carbon atoms inclusive, and AR is an aryl radical. A method for making such compounds and lubricant compositions containing such compounds are also disclosed.

14 Claims, No Drawings

HYDROGEN PERFLUOROALKYLAROMATIC ETHERS AND RELATED COMPOSITIONS AND METHODS

TECHNICAL FIELD

This invention relates generally to hydrogenperfluoroalkyl aromatic ethers which are useful as lubricant base stocks or lubricant additives and compositions and methods related to these ethers.

BACKGROUND OF THE INVENTION

The demands placed on lubricants are currently undergoing significant changes. Engines are being developed for automotive and aeronautic applications that have requirements dramatically different from those of engines currently in use. It is anticipated that these engines will operate at temperatures exceeding 250° C. and will be constructed using materials new or different from those currently in use. Thus, what is needed are novel compounds useful as lubricant base stocks or lubricant additives that are stable at the high use temperatures while possessing the other properties required of lubricants.

Being stable at high use temperatures means that the desired lubricating compounds would (1) have low reactivity at elevated temperatures, e.g., be less oxidative, less hydrolyzable, less reactive to bases, and less polymerizable, (2) experience little or no decomposition at elevated temperatures, and (3) have relatively low volatility and high boiling points.

It is desirable that the new lubricating compounds be highly soluble in organic oils and greases if they are to be used as lubricant additives. It would also be beneficial if the new lubricating compounds could be prepared by simple methods and in high yields.

It is, therefore, a primary object of this invention to provide new compounds and a method for making such compounds which (1) are useful as lubricant base stocks or lubricant additives, (2) are stable at high temperatures, (3) are highly soluble in organic oils and/or greases, and (4) which can be prepared by relatively simple methods and in high yields.

It is another object of this invention to provide lubricant compositions containing such compounds.

SUMMARY OF THE INVENTION

In accordance with a preferred embodiment of the invention, these and other objects and advantages are addressed as follows. A compound having the structure:

$$R^1-R_f-O-Ar-R^2$$

is disclosed wherein:

$R^1$ is a monovalent radical selected from the group consisting of fluoride, unsubstituted aryloxys, substituted aryloxys, unsubstituted arylthios, substituted arylthios, perfluoroalkoxys, and perfluoro (3, 6-dimethyl-1, 4-dioxanyl-2-oxy), $R^2$ is a monovalent radical selected from the group consisting of hydrogen, halides, cyano, nitro, unsubstituted alkyls having from 1 to 10 carbon atoms inclusive, perfluoroalkyls having from 1 to 10 carbon atoms inclusive, perfluoroalkoxys having from 1 to 10 carbon atoms inclusive, substituted and unsubstituted hydrogen perfluoroalkoxy aryloxys, substituted and unsubstituted hydrogen perfluoroalkoxy arylthios, unsubstituted alkoxys having from 1 to 8 carbon atoms inclusive, unsubstituted aryls, substituted aryls, unsubstituted aryloxys, substituted aryloxys, unsubstituted alkylthios, substituted arylthios, unsubstituted arylthios, substituted and unsubstituted arylketones, substituted and unsubstituted arylsulfones, and substituted and unsubstituted alkylcarboxys, $R_f$ is a hydrogen perfluoroalkyl divalent radical having from 2 to 10 carbon atoms inclusive, and Ar is an aryl radical.

Lubricant compositions containing the above-described compounds also form part of the invention.

The invention also includes a method for forming a lubricating compound, comprising reacting (a) a compound having the structure:

$$R^1-R_f-O-Ar-C(O)PhF$$

wherein $R^1$ is a monovalent radical selected from the group consisting of fluoride, unsubstituted aryloxys, substituted aryloxys, unsubstituted arylthios, substituted arylthios, perfluoroalkoxys, and perfluoro (3, 6-dimethyl-1, 4-dioxanyl-2-oxy), $R_f$ is a hydrogen perfluoroalkyl divalent radical having from 2 to 10 carbon atoms inclusive, and Ar is an aryl radical, with (b) a reactant selected from the group consisting of alcohols, metallic salts of alcohols, and mercaptans.

DETAILED DESCRIPTION OF THE INVENTION

The compounds of this invention are hydrogen-perfluoroalkyl aromatic ethers having the following structure:

$$R^1-R_f-O-Ar-R^2.$$

$R^1$ is a monovalent radical selected from the group consisting of fluoride, unsubstituted aryloxys, substituted aryloxys, unsubstituted arylthios, substituted arylthios, perfluoroalkoxys, and perfluoro (3, 6-dimethyl-1, 4-dioxanyl-2-oxy), $R^2$ is a monovalent radical selected from the group consisting of hydrogen, halides, cyano, nitro, unsubstituted alkyls having from 1 to 10 carbon atoms inclusive, perfluoroalkyls having from 1 to 10 carbon atoms inclusive, perfluoroalkoxys having from 1 to 10 carbon atoms inclusive, substituted and unsubstituted hydrogen perfluoroalkoxy aryloxys, substituted and unsubstituted hydrogen perfluoroalkoxy arylthios, unsubstituted alkoxys having from 1 to 8 carbon atoms inclusive, unsubstituted aryls, substituted aryls, unsubstituted aryloxys, substituted aryloxys, unsubstituted alkylthios, substituted arylthios, unsubstituted arylthios, substituted and unsubstituted arylketones, substituted and unsubstituted arylsulfones, and substituted and unsubstituted alkylcarboxys.

The $R_f$ radical is a straight-chain or branched hydrogen perfluoroalkyl divalent and alkyl radical having no unsaturation and from 2 to 10 carbon atoms inclusive. Preferably, $R_f$ has from 2 to 6 carbon atoms inclusive and, more preferably, 3 carbon atoms. The $R_f$ radical may be bonded to the aryloxy structure at any one of its carbon atoms. The hydrogen of the $R_f$ radical may be bonded to any one of the carbon atoms of the alkyl radical. Typically, however, the aryloxy is bonded to the alpha carbon of the $R_f$ radical, and the hydrogen is bonded to the beta carbon.

Ar is an aryl radical and may be, for example, phenyl, biphenylyl, naphthyl, pyridyl, pyrimidinyl, triazenyl, and the like.

More specifically, $R^1$ may be $-OPhR^2z$; $-OXOR_fOPhR^2z$; $-SPhR^2z$; $-ONpR^2z$; $-OPyR^2z$; and $-(OCF_2CFR^3)_mF$, wherein:

$R^3$ is a monovalent radical selected from the group consisting of $-F$ and perfluoroalkyls, X is a divalent radical selected from the group consisting of -Ph- and PhQPh, Q is a divalent radical selected from the group consisting of $-CH_2-$, $-C(CF_3)_2-$, $-C(CH_3)_2-$, $-SO_2-$, $-CO-$, $-S-$, $-O-$, $-PhC(CF_3)_2Ph-$; and $-PhC(CH_3)_2Ph-$;

Ph is the phenyl radical, Np is the naphthyl radical, Py is the pyridyl radical, m is from 1 to 20 inclusive, preferably from 1 to 10 inclusive, and z is from 1 to 2 inclusive.

$R^2$ may be $-(OPh)_n$; $-OPhR^4z$; $-OR_fOPhR^4z$; $-OR_fSPhR^4z$; $-OR_fONpR^4z$; $-OR_fOPyR^4z$; and $-C(O)PhR^5z$; wherein:

$R^4$ is a monovalent radical selected from the group consisting of hydrogen, halides, cyano, nitro, unsubstituted alkylthios, substituted alkylthios, unsubstituted alkyls, perfluoroalkyls, and perfluoroalkoxys, $R^5$ is a monovalent radical selected from the group consisting of fluoride, unsubstituted aryloxys, substituted aryloxys, unsubstituted arylthios, and substituted arylthios, Ph is the phenyl radical, Np is the naphthyl radical, Py is the pyridyl radical, n is from 1 to 4 inclusive, and z is from 1 to 2 inclusive. "C(O)" e.g. in the radical $-C(O)$ $pHR^5z$ refers to a ketone.

Specific examples of $R^5$ include $-OPhR^7z$, $-SPhR^7z$, $-OPyR^7z$, and $-ONpR^7z$, wherein $R^7$ is a monovalent radical selected from the group consisting of hydrogen, halides, nitro, cyano, unsubstituted alkyls, substituted alkyls, unsubstituted alkoxys, substituted alkoxys, unsubstituted aryls, and substituted aryls, and unsubstituted aryloxys.

When a radical, such as $R^2$, occurs twice in the same compound, the two radicals may be the same or different. For example, $R^2$ occurs twice in the compound $R^1-R_fO-Ar-R^2$ where $R^1$ is $-OPhR^2z$. The two $R^2$'s in this compound may be the same or different.

Preferably, the compounds of this invention are stable up to temperature of at least about 300° C. as measured using a differential scanning calorimeter (DSC) at 200 psi. Generally, the DSC test indicates the temperature at which degradation of the compound begins.

The compounds of this invention may be liquid or solid at room temperature. If the compound is to be used as a lubricant base stock and not as a lubricant additive, the compound should be a liquid at the temperature of use.

Preferred compounds of the invention include (a) benzophenones having the structure:

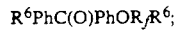

(b) sulfides having the structure:

(c) benzosulfones having the structure:

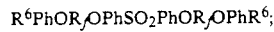

(d) benzene-containing compounds having the structure:

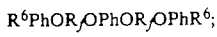

(e) bisphenol derivatives having the structure:

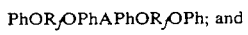

and (f) ethers having the structure:

wherein $R^6$ is a monovalent radical selected from the group consisting of hydrogen, halides, substituted and unsubstituted alkyls, unsubstituted and substituted alkoxys, substituted and unsubstituted aryloxys, and substituted and unsubstituted arylthios, $R_f$ is defined as hereinbefore, A is a divalent radical selected from the group consisting of $-C(CF_3)_2-$ and $-C(CH_3)_2-$, and Ph is the phenyl radical.

More specifically, preferred compounds include (a) benzophenones selected from the group consisting of 4-fluoro-4'-(1, 1, 2, 3, 3, 3-hexafluoropropoxy)benzophenone;

4-fluoro-4'-(1-(3-methoxyphenoxy)-1,2,3,3,3-pentafluoropropoxyl)benzophenone;

4-fluoro-4'-(1-(3-phenoxyphenoxy)-1,2,3,3,-pentafluoropropoxy)benzophenone;

4-phenylthio-4'-(1-(3phenoxyphenoxy)-1,2,3,3,3-pentafluoropropoxy)benzophenone;

4- fluoro-4'- (1-phenylthio-1,2,3,3,3-pentafluoropropoxy)benzophenone;

4-(3-trifluoromethylphenoxy)-4'-(1-(3-phenoxyphenoxy)-1,2,3,3,3-pentafluoropropoxy)benzophenone; and 4-(3-phenoxyphenoxy)-4'-(1-phenoxy-1,2,3,3,3-pentafluoropropoxy)benzophenone;

(b) sulfides selected from the consisting of bis(4-(3-methoxyphenoxy-1,2,3,3,3-pentafluoropropoxy)phenyl) sulfide; and bis (4-(1-phenoxy-1,2,3,3,3-pentafluoropropoxy)-phenyl)sulfide;

(c) bis (4-(1-phenoxy-1,2,3,3,3-pentafluoropropoxy)phenyl) benzosulfone;

(d) benzene-containing compounds selected from the group consisting of 1,3-bis(1-(3-phenoxyphenoxy)-1,2,3,3,3-pentafluoropropoxy)benzene; and 1,3-bis(1-phenoxy-1,2,3 3-pentafluoropropoxy) benzene;

(e) bisphenol derivatives selected from the group consisting of 2,2-bis(4-(1-phenoxy-1,2,3,3,3-pentafluoropropoxy)-phenyl) propane; and 2,2-bis(4-(1-phenoxy-1,2,3,3,3-pentafluoropropoxy)-phenyl)-1,1,1,3,3,3-hexafluoropropane; and (f) ethers selected from the group consisting of bis(4-(1-(4-(1,1-dimethylethylphenoxy)-1,2,3,3,3-pentafluoropropoxy)phenyl)ether; and bis(4-(1-(3-phenoxyphenoxy)-1,2,3,3,3-pentafluoropropoxy)phenyl) ether.

Other preferred compounds of the invention include 1,1,1,3,3,3-hexafluoro-2,2-bis(4-(1,2,3,3,3-pentafluoro-1-phenoxypropoxy)phenyl)propane, 1,3-bis(4-(1,2,3,3,3- pentafluoro-1-phenoxypropoxy)benzene, 1-(3-phenoxyphenoxy)-1-(3-(3-phenoxyphenoxy)phenoxy)-1,2,3,3,3-pentafluoropropane, 4-phenylthio-4'-(1-(3-methoxyphenoxy)-1,2,3,3,3-pentafluoropropoxy)benzophenone, 4-phenoxy-4'-(1-phenoxy-1,2,3,3,3-pentafluoropropoxy)benzophenone, 4-(3-phenoxyphenoxy)-4'-(1,1,2,3,3,3-hexafluoropropoxy)benzophenone, and 4-(2-pyridyloxy)-4'-(1-phenoxy-1,2,3,3,3-pentafluoropropoxy)benzophenone.

A general class of preferred compounds is 4-fluoro-4'-(1-(substituted aryloxy)-hydrogenperfluoroalkoxy) benzophenones having the structure:

wherein R¹ is a monovalent radical selected from the group consisting of fluoride, unsubstituted aryloxys, substituted aryloxys, unsubstituted arylthios, substituted arylthios, perfluoroalkoxys, and perfluoro (3, 6-dimethyl-1, 4-dioxanyl-2-oxy), R_f is a hydrogen perfluoroalkyl divalent radical having from 2 to 10 carbon atoms inclusive, and Ar is an aryl radical. Specific examples of such benzophenones include 4-fluoro-4'- (1-(3-methoxyphenoxy)-1,2,3,3,3-pentafluoropropoxy)benzophenone; 4-fluoro-4'-(1,1,2,3,3,3-hexafluoropropoxy) benzophenone; 4-fluoro-4'-(1,2,3,3,3-pentafluoro-1-phenylthiopropoxy)benzophenone, 4-fluoro-4'-(1,2,3,3,3-pentafluoro-1-phenylpropoxy) benzophenone, 4-fluoro-4'-(1-(3-phenoxyphenoxy)-1,2,3,3,3-pentafluoropropoxy) benzophenone, 4-fluoro-4'-(1-(6-chloropyridinyloxy)-1,2,3,3,3-pentafluoropropoxy)benzophenone, and 4-fluoro-4'-(1-(2-naphtyloxy)-1,2,3,3,3-pentafluoropropoxy) benzophenone. These compounds have utility not only as lubricants themselves but also as intermediates for the production of new extended-temperature-range lubricating compounds.

Generally, the compounds of this invention are made by the base-catalyzed addition of hydroxy-substituted aryl compounds, such as phenols, to terminal perfluoroolefins, such as aryloxyperfluoroalkenes or arylthioperfluoroalkenes.

The terminal perfluoro olefins may be prepared by any one of a number of known methods disclosed in, e.g., Nippon Kaoaku Kai-shi, Vol. 1975, No. 2, pp. 311-315; U.S. Pat. No. 3,180,895; and Japanese patent disclosures 50-117727 and 62-153236, which documents are hereby incorporated by reference.

A preferred method of making a terminal perfluoro olefin, such as an aryloxy perfluoroalkene, includes (a) reacting a phenol with sodium in a solvent such as a glyme to form a phenoate, (b) reacting the phenoate with a perfluoroalkene at subzero temperatures, e.g., −40° C., and (c) purifying the resulting product by distillation. Alternatively, a dihydroxybenzene or a bisphenol may be used in place of the phenol. In these later cases, two moles of perfluoroalkene react to each mole of dihydroxybenzene or bisphenol.

Preferably, the reaction between the hydroxy-substituted aryl compound and the terminal perfluoro olefin is performed in a dipolar aprotic solvent, such as acetonitrile, dimethylsulfoxide, dimethylformamide, N-methylpyrrolidone, or diphenyl sulfone. Dimethylformamide and acetonitrile are the most preferred solvents. In some reactions, such as those which use a highly perfluorinated olefin, it is desirably to use a co-solvent, such as a chlorofluorohydrocarbon, e.g. "FREON" 113. "FREON" products are available from E. I. du Pont de Nemours & Co., Inc., Wilmington, Del., owner of the trademark "FREON".

Many types of bases may be employed in the reaction. Examples of suitable bases include alkali carbonates, alkali hydrogen carbonates, alkaline earth carbonates, alkali hydroxides, alkaline earth metal hydroxides, and amine bases, such as triethylamine. The most preferred bases are weak bases, such as potassium carbonate and triethylamine.

A catalytic amount of the base, e.g., about 0.05 to about 0.2 molar equivalent per 100 moles of the terminal perfluoroolefin, is sufficient for the reaction to proceed. However, a molar equivalent or more of the base is preferred for a significantly shorter reaction time.

The reaction is desirably performed at ambient conditions, but may be performed at temperatures from about 0° to about 200° C. at atmospheric, sub-atmospheric or superatmospheric pressures.

The reaction time depends on the variables of the reaction, such as the nature of the solvent, the amount of base employed, and the temperature. Typically, the reaction time ranges from about to about 24 hours at ambient temperature.

As mentioned hereinabove, a class of compounds of the invention, namely, the 4-fluoro-4'-(1-(substituted aryloxy)-hydrogenperfluoroalkoxy) benzophenones, may be used as intermediates for the production of new extended-temperature-range lubricating compounds. These benzophenones may be reacted with alcohols, metallic salts of alcohols, or mercaptans under basic conditions, preferably in a dipolar aprotic solvent. Suitable bases and amounts for catalyzing the reaction and suitable dipolar aprotic solvents are the same as those listed hereinabove. The reaction may be performed at temperatures ranging from about 0°-200° C., but preferably at about 20°-100° C. After the reaction is complete, the solid byproducts are filtered out, and low boiling materials are removed by distillation. The product may be purified further by distillation techniques.

The compounds of this invention are useful as lubricants over extended temperature ranges. They may be used alone and also may be used in conjunction with various additives to improve their performance. Additionally, they may themselves be used as additives with other base stocks.

When used as an additive to a base stock, the compounds of the present invention must be compatible with the base stock. By compatible, it is meant that the compounds of the present invention may be readily dispersed or dissolved in the base stock, either with or without the addition of an appropriate surfactant. Examples of known base stocks useful in conjunction with the compounds of this invention include organic oils and greases well known to those skilled in the art. When the compounds of the present invention are used as additives to conventional, compatible base stocks, it is preferred that the base stocks are polyglycols, polyphenyl ethers and polyol esters. It is more preferred that the base stocks are polyphenyl ethers, such as 5P4E which is a polyphenyl ether having five phenyl groups and four ether linkages. Other preferred base stocks include polyol esters such as pentaerythritol tetra C_{5-9} esters (PET).

Lubricant compositions of this invention comprise from about 0.1 to about 100 weight percent of the compounds of the invention. That is, the compounds of this invention may be used as a lubricant base stock or they may be used as additives with other base stocks.

When the compounds of this invention are used as lubricant additives, it is preferred that they are used in amounts of at least about 0.5 weight percent, more preferably at least about 50 weight percent. It is also preferred that the compounds of the present invention, when used as additives, are used in amounts of no greater than about 50 weight percent, preferably no greater than about 20 weight percent.

As discussed above, the compounds of the present invention may be used as lubricant base stocks themselves, either alone or with the addition of additives known in the art. The preferred additives are functional additives which can increase stability and/or provide resistance to corrosion. When used as the lubricant base stock with additives, it is preferred that the compound of this invention comprise at least about 50 weight percent, more preferably at least about 95 weight percent of the composition with one or more additives making up the remainder of the lubricant composition. Additionally, the compounds of this invention may be blended with other base stocks to prepare lubricants.

Thus, there is provided in accordance with the present invention, new lubricating compounds which are stable at high temperatures, which are highly soluble in organic oils and/or greases, and which may be prepared by relatively simple methods in high yields. Also provided by this invention are lubricant compositions containing such lubricating compounds and a method for preparing such lubricating compounds.

The following examples are illustrative only and should not be construed as limiting the invention which is properly delineated in the appended claims.

EXAMPLES

Example 1

Preparation of
1,3-bis(1-phenoxy-1,2,3,3,3-pentafluoropropoxy)benzene 11 g 1,3-dihydroxybenzene, 15 g potassium carbonate, 100 ml dimethylformamide, and 20 g 1-(1,2,3,3,3-pentafluoro-1-propenyloxy)benzene were added to a flask and reacted by stirring at room temperature for six hours. 200 ml methylene chloride and 500 mls water were admixed with the reacted mixture. The reacted mixture was phase-separated from the aqueous phase and washed and separated two more times with 100 ml water per wash. The washed reacted mixture was then dried over sodium sulfate, filtered, and distilled to remove low-boiling compounds. The distilled product was further distilled to produce the desired benzene having a boiling point of 175° C. at 0.6 mm Hg.

Example 2

Preparation of 1,1,1,3,3,3-hexafluoro-2,2-bis
(4-(1,2,3,3,3-pentafluoro-1-phenoxypropoxy)phenyl)-propane 17 g 4,4'-(hexafluoroisopropylidene) diphenol, 100 ml dimethylformamide, 14 g potassium carbonate, and 30 g 1-phenoxy perfluoropropene were added to a flask and reacted by stirring for four hours at room temperature. The mixture was then stirred for an additional hour at 50° C., then cooled to room temperature. After cooling, 100 ml methylene chloride and 250 ml water were admixed with the reacted mixture. The reacted mixture was separated from the aqueous phase by phase separation techniques. The reacted mixture was washed again with 150 ml water and separated from the aqueous phase, dried over sodium sulfate, and filtered. The product was purified from the reacted mixture by distilling to 240°–280° C. to remove the low-boiling compounds. NMR spectra indicated the product to be about 90% of the desired propane. The process resulted in a 25% yield. Differential scanning calorimetry of the product indicated that the propane product is stable up to 340° C. under 200 psi oxygen pressure, suggesting a high degree of thermo-oxidative stability.

Example 3

Preparation of
1-(3-phenoxyphenoxy)-1-(3-(3-phenoxyphenoxy)-phenoxy-1,2,3,3,3-pentafluoropropane 7 g 3-phenoxy-3-phenoxyphenol, 10 g 1-(3-phenoxyphenoxy)perfluoropropene, 100 ml dimethylformamide, and 4 g potassium carbonate were added to a flask and reacted by stirring for three hours at room temperature. The reacted mixture was then allowed to stand overnight. 250 ml water and 200 ml methylene chloride were admixed into the reacted mixture. The reacted mixture layer was separated from the aqueous layer and again washed with 200 ml water. The reacted mixture layer was again separated from the aqueous layer, dried over sodium sulfate, filtered, and distilled to produce an oil having a boiling point of about 280° C. at 0.5 mm Hg. The process resulted in a 47% yield of the desired propane. Differential scanning calorimetry of the product indicated that the ethane product is stable up to 343° C. under 200 psi oxygen pressure, suggesting a high degree of thermo-oxidative stability.

Example 4

Preparation of
1-(m-(m-phenoxyphenoxy-m-phenoxyphenoxy)phenoxy)-2-H-2-(3,6,9-trimethyl-1,4,7-trioxa-1-perfluorononyl)-1,1,2-trifluoroethane 3.2 g 1-(m-(m-phenoxyphenoxy-m-phenoxyphenoxy))phenol, 5.0 g 2-(3,6,9-trimethyl-1,4,7-trioxa-1-perfluorononyl)-1,1,2-trifluoroethylene, 2.0 g potassium carbonate and 15 ml dimethylformamide were reacted by stirring the ingredients together for 12 hours at ambient temperature. 50 ml water and 50 ml ethyl acetate were admixed into the reacted mixture for a few minutes. The reacted mixture layer was then separated from the aqueous layer, dried over magnesium sulfate, and solvent-evaporated. Flash chromotography indicated that the product was the desired ethane prepared at 95.5% yield. Differential scanning calorimetry of the product indicated that the ethane product is stable up to 470° C. under 200 psi of oxygen pressure, suggesting a high degree of thermo-oxidative stability.

Example 5

Preparation of
1-(m-methoxyphenoxy)-2-H-2-(3,6,9-trimethyl-1,4,7-trioxa-1-perfluorononyl)-1,1,2-trifluoroethane 11.6 g m-methoxyphenol, 56.5 g 2-(3,6,9-trimethyl-1,4,7-trioxa-1-perfluorononyl)-1,1,2-trifluoroethylene, 18 g potassium carbonate, and 100 ml acetonitrile were stirred together for 16 hours at ambient temperature to allow the ingredients to react. Water washing and extraction with ethyl ether as described in Example 4 was completed. Yield of the desired ethane was 98%.

Example 6

Preparation of
1-(m-hydroxyphenoxy)-2-H-2-(3,6,9-trimethyl-1,4,7-trioxa-1-perfluorononyl)-1,1,2-trifluoroethane 50 g boron tribromide are added dropwise to a mixture of 67.0 g of the ethane product form Example 5 and 200 ml methylene chloride held at a temperature of −10° C. in a nitrogen atmosphere. The mixture was stirred at ambient temperature for 2 hours to allow the ingredients to react. The mixture was then quenched by adding ice and acidified with 200 ml 2N HCl. The product was extracted with ether and distilled at 110°–120° C. and 0.5 mm Hg. Yield of the desired ethane was 87.6%.

Example 7

Preparation of
1-(m-(m-phenoxyphenoxy-m-phenoxyphenoxy)phenoxy)-2-H-2-(perfluoro-3,6-dimethyl-1,4-dioxanyl-2-oxy)-1,1,2-trifluoroethane 1-(m-(m-phenoxyphenoxy-m-phenoxyphenoxy))-phenol and perfluoro-2-ethenyloxy-(3,6-dimethyl)-1,4-dioxane were reacted according to the procedure in Example 4, resulting in a 92% yield of the desired ethane. The dioxane was prepared by the pyrolysis of perfluoro -(3,6-dimethyl-1,4-dioxanyl-2-oxy) propionic acid potassium salt which, in turn, was prepared by the hydrolysis of the corresponding acid fluoride made according to U.S. Pat. No. 4,033,984. The boiling point of the ethane product was determined to be 230°–240° C. at 1 mm Hg.

Example 8

Preparation of 4-fluoro-4' (1,1,2,3,3,3-hexafluoropropoxy)benzophenone 43 g 4-fluoro-4'-hydroxybenzophenone, 30 g potassium carbonate, and 400 ml acetonitrile were mixed in a flask and cooled to about 0° C. 45 g perfluoropropene were bubbled into the cooled mixture over about a 45-minute period. After the addition of the perfluoropropene, the mixture was stirred for four hours while it warmed to room temperature. Solids in the mixture were removed by filtration, and acetonitrile was removed by distillation. The product was distilled again at 160°–165° C./0.5 mm Hg pressure. Gas chromatography confirmed that the product was the desired benzophenone.

Example 9

Preparation of
4-fluoro-4'(1-(3-methoxyphenoxy)-1,2,3,3,3-pentafluoropropoxy)benzophenone 35 g 3-methoxyphenoxyperfluoropropene, 19 g potassium carbonate, 22 g 4-hydroxy-4'-fluorobenzophenone, and 150 ml dimethylformamide were reacted by stirring together for 6 hours at room temperature, followed by eight hours at 70°–75° C. Solids in the reacted mixture were removed by filtration, and low-boiling compounds were removed by distillation at 150° C./0.5 mmHg. The resulting product was shown by gas chromatography to be the desired benzophenone, having a boiling point of about 220° C. at 0.5 mm Hg.

Example 10

Preparation of
4-fluoro-4'-(1-(3-phenoxyphenoxy)-1,2,3,3,3-pentafluoropropoxy)benzophenone 22 g 4-hydroxy-4'-fluoro-benzophenone, 19 g potassium carbonate, 40 g 3-phenoxyphenoxy perfluoropropene, and 150 ml dimethylformamide were reacted by stirring the ingredients together for eight hours at 80°–90° C. After cooling the reaction mixture to room temperature, the solids in the reaction mixture were removed by filtration, and the solvent was distilled off under reduced pressure at 100° C. The product was further distilled at 212°–250° C. and 0.5 mm Hg. The process resulted in a 61% yield of the desired benzophenone product, confirmed by gas chromatography.

Example 11

Preparation of
4-phenylthio-4'-(1-(3-methoxyphenoxy)-1,2,3,3,3-pentafluoropropoxy)benzophenone 33 g 4-fluoro-4'-(1-(3-methoxyphenoxy)-1,2,3,3,3-pentafluoro-propoxy)benzophenone, 10 g potassium carbonate, 7.7 g thiophenol, and 100 ml dimethylformamide were stirred together for eight hours at 100° C., then allowed to cool to room temperature. After cooling, the solids were removed from the mixture by filtration, and the low boilers were removed by distillation at 200° C./0.5 mm Hg. The resulting product was distilled at 240°–300° C./0.5 mm Hg. NMR spectra and gas chromatography confirmed that the desired benzophenone was prepared.

EXAMPLE 12

Evaluation of lubricating properties of various hydrogenperfluoroalkyl aromatic ethers of this invention The anti-wear and extreme pressure characteristics of compositions containing some of the compounds of this invention were measured using a four-ball test using a Falex friction and wear tester, available from Faville-Levally Corp. Downers Grove, Ill. The compositions tested included mixtures of polyphenylether 5P4E and a selected level of the compound of the invention. Table 1 provides the particular compound of the invention employed and the weight percent added to the polyphenylether 5P4E.

In Table 1, Compound #1 refers to bis(4-(3-methoxyphenoxy-1,2,3,3,3-pentafluoropropoxy)phenyl)sulfide, Compound #2 refers to 1,3-bis(1-(3-phenoxyphenoxy)-1,2,3,3,3-pentafluoropropoxy)benzene, Compound #3 refers to bis(1-(4-t-butylphenoxy)-1,2,3,3,3-pentafluoropropoxy phenyl)ether, Compound #4 refers to (4-(1-phenoxy)-1,2,3,3,3-pentafluoro-propoxy)phenyl)sulfide, Compound #5 refers to 4, 4'-bis(1-phenyl-1,2,3,3,3-pentafluoropropoxy)benzosulfone, and Compound #6 refers to 4-phenylthio-4'(1'-(3-methoxyphenoxy)-1,2,3,3,3-pentafluoropropoxy) phenylbenzophenone.

The four ball-bearing balls used in the test were made of M50 steel. The test load was 15 kg (33.1 lbs), and the temperature was held at 300° C. The test speed was 1200 rpm, and each test was run for one hour. About 60 cubic centimeters of fluid were used for each test. During each test, the torque as a function of the wear cycles was monitored on a real time data acquisition basis for data analysis to yield the coefficient of friction. Optical microscope pictures of the bearing balls were taken at the test completion and scar diameter was measured from these pictures. Table 1 provides the wear scar value and coefficient of friction of each test run.

TABLE 1

| Compound # | Wt % In Oil | Wear Scar Value (mm) | Coefficient of Friction |
|---|---|---|---|
| None | 0.0 | 2.61 | 0.197 |
| 1 | 0.3 | 0.43 | 0.065 |
| 1 | 5.0 | 0.34 | 0.041 |
| 1 | 9.5 | 0.29 | 0.036 |
| 1 | 35.0 | 0.28 | 0.057 |
| 2 | 1.0 | 2.02 | 0.158 |
| 3 | 1.0 | 1.62 | 1.163 |
| 4 | 1.0 | 0.55 | 0.068 |
| 5 | 1.0 | 1.67 | 0.120 |
| 6 | 1.0 | 1.62 | 0.180 |

While our invention has been described in terms of a few specific embodiments, it will be appreciated that other embodiments could readily be adapted by one skilled in the art. Accordingly, the scope of our invention is to be considered limited only by the following claims.

We claim:

1. A compound having the structure:

$$R^1-R_f-O-Ar-R^2$$

wherein
R$^1$ is a monovalent radical selected from the group consisting of aryloxys, arylthios, and perfluoro (3,6-dimethyl-1,4-dioxanyl-2oxy),
R$^2$ is a monovalent radical selected from the group consisting of hydrogen, halides, cyano, nitro, alkyls having from 1 to 10 carbon atoms inclusive, perfluoroalkyls having from 1 to 10 carbon atoms inclusive, perfluoroalkoxys having from 1 to 10 carbon atoms inclusive, hydrogen perfluoroalkoxy aryloxys, hydrogen perfluoroalkoxy arylthios, alkoxys having from 1 to 8 carbon atoms inclusive, aryls, aryloxys, alkylthios, arylthios, arylketones, arylsulfones, and alkylcarboxys,
R$_f$ is a hydrogen perfluoroalkyl divalent radical having from 2 to 10 carbon atoms inclusive, and
Ar is an aryl radical.

2. The compound of claim 1, wherein
R$^1$ is selected from the group consisting of —OPhr$^2_z$; —OXOR$_f$OPhR$^2_z$; —SPhR$^2_z$; —ONpR$^2_z$; and —OPyR$^2_z$;
X is a divalent radical selected from the group consisting of —Ph— and —PhQPh—,
Q is a divalent radical selected from the group consisting of —CH$_2$—, —C(CF$_3$)$_2$—, —C(CH$_3$)$_2$—, —SO$_2$—, —CO—, —S—, —O—, —PhC(CF$_3$)$_2$Ph—; and —PhC(CH$_3$)$_2$Ph—;
Ph is the phenyl radical,
Np is the naphthyl radical,
Py is the pyridyl radical,
m is from 1 to 20 inclusive, and
z is from 1 to 2 inclusive.

3. The compound of claim 1,
wherein R$^2$ is a monovalent radical selected from the group consisting of —(OPh)$_n$; —OPhR$^4_z$; —OR$_f$OPhR$^4_z$; —OR$_f$SPhR$^4_z$; —OR$_f$ONpR$^4_z$; —OR$_f$OPyR$^4_z$; and —C(O)PhR$^5_z$;
R$^4$ is a monovalent radical selected from the group consisting of hydrogen, halides, cyano, nitro, alkylthios, alkyls, perfluoroalkyls, and perfluoroalkoxys,
R$^5$ is a monovalent radical selected from the group consisting of fluoride, aryloxys, arylthios,
Ph is the phenyl radical,
Np is the naphthyl radical,
Py is the pyridyl radical,
n is from 1 to 4 inclusive, and
z is from 1 to 2 inclusive.

4. The compound of claim 1, wherein R$^2$ is —C(O)PhF.

5. The compound of claim 1, wherein R$_f$ has from 2 to 6 carbon atoms inclusive.

6. The compound of claim 1, wherein R$_f$ is a hydrogen perfluoropropyl divalent group.

7. The compound of claim 1, wherein the compound is stable up to a temperature of at least 300° C.

8. The compound of claim 1, wherein the compound is selected from the group consisting of
(a) a benzophenone having the structure:

R$^6$PhC(O)PhOR$_f$R$^6$;

(b) a sulfide having the structure:

R$^6$PhOR$_f$OPhSPhOR$_f$OPhR$^6$;

(c) a benzosulfone having the structure:

R$^6$PhOR$_f$OPhSO$_2$PhOR$_f$OPhR$^6$;

(d) a benzene-containing compound having the structure:

R$^6$PhOR$_f$OPhOR$_f$OPhR$^6$;

(e) a bisphenol derivative having the structure:

PhOR$_f$OPhAPhOR$_f$OPh; and (f) an ether having the structure:

R$^6$PhOR$_f$OPhOPhOR$_f$OPhR$^6$, wherein
R$^6$ is a monovalent radical selected from the group consisting of hydrogen, halides, alkoxys, aryloxys, and arylthios,
R$_f$ is a hydrogen perfluoroalkyl divalent radical having from 2 to 10 carbon atoms inclusive,
A is a divalent radical selected from the group consisting of —C(CF$_3$)$_2$— and —C(CH$_3$)$_2$—, and
Ph is the phenyl radical.

9. The compound of claim 1, wherein the compound is selected from the group consisting of:
(a) a benzophenone selected from the group consisting of
4-fluoro-4'-(1-(3-methoxyphenoxy)-1,2,3,3,3-pentafluoropropoxy)benzophenone;
4-fluoro-4'-(1-(3-phenoxyphenoxy)-1,2,3,3,3-pentafluoropropoxy)benzophenone;
4-phenylthio-4'-(1-(3-phenoxyphenoxy)-1,2,3,3,3-pentafluoropropoxy)benzophenone;
4-fluoro-4'-(1-phenylthio-1,2,3,3,3-pentafluoropropoxy)benzophenone;
4-(3-trifluoromethylphenoxy)-4'-(1-(3-phenoxyphenoxy)-1,2,3,3,3-pentafluoropropoxy)benzophenone; and 4-(3-phenoxyphenoxy)-4'-(1-phenoxy-1,2,3,3,3-pentafluoropropoxy)benzophenone;
(b) a sulfide selected from the group consisting of
bis (4-(3-methoxyphenoxy-1,2,3,3,3,-pentafluoropropoxy)phenyl) sulfide; and
bis (4-(1phenoxy-1,2,3,3,3-pentafluoropropoxy)phenyl)sulfide;
(c) a benzosulfone including bis(4-(1-phenoxy-1,2,3,3,3-pentafluoroporpoxy)phenyl) benzosulfone;
(d) a benzene-containing compound selected from the group consisting of
1,3-bis(1-(3-phenoxypehnoxy)-1,2,3,3,3-pentafluoropropoxy)benzene; and
1,3-bis(1-phenoxy-1,2,3,3,3-pentafluoropropoxy) benzene;
(e) a bisphenol derivative selected from the group consisting of
2,2-bis(4-(1-phenoxy-1,2,3,3,3-pentafluoropropoxy)phenyl) propane; and
2,2-bis(4-(1-phenoxy-1,2,3,3,3-pentafluoropropoxy)phenyl)-1,1,1,3,3,3-hexafluoropropane; and
(f) an ether selected from the group consisting of
bis(4-(1-(4-(1,1-dimethylethylphenoxy)-1,2,3,3,3-pentafluoropropoxy)phenyl)ether; and
bis(4-(1-(3-phenoxyphenoxy)-1,2,3,3,3-pentafluoropropoxy)phenyl) ether.

10. A lubricant composition comprising from at least about 0.1 to about 100 weight percent of the compound of claim 1.

11. A lubricant composition comprising from about 0.5 to about 50 weight percent of the compound of claim 1.

12. A lubricant composition comprising from about 5 to about 20 weight percent of the compound of claim 1.

13. A lubricant composition comprising at least about 50 weight percent of the compound of claim 1.

14. A lubricant composition comprising at least about 95 weight percent of the compound of claim 1.

* * * * *